US011253279B2

(12) United States Patent
Follmer

(10) Patent No.: US 11,253,279 B2
(45) Date of Patent: Feb. 22, 2022

(54) APPARATUS, SYSTEM, AND METHOD FOR VASCULATURE OBSTRUCTION REMOVAL

(71) Applicant: Progressive NEURO, Inc., Santa Clara, CA (US)

(72) Inventor: Brett Allen Follmer, Santa Clara, CA (US)

(73) Assignee: Progressive NEURO, Inc.

( * ) Notice: Subject to any disclaimer, the term of this patent is extended or adjusted under 35 U.S.C. 154(b) by 218 days.

(21) Appl. No.: 16/572,150

(22) Filed: Sep. 16, 2019

(65) Prior Publication Data

US 2020/0155180 A1 May 21, 2020

Related U.S. Application Data

(60) Provisional application No. 62/767,852, filed on Nov. 15, 2018.

(51) Int. Cl.
*A61B 17/221* (2006.01)
*A61M 39/10* (2006.01)
(Continued)

(52) U.S. Cl.
CPC ....... *A61B 17/221* (2013.01); *A61M 39/1011* (2013.01); *A61B 17/22031* (2013.01);
(Continued)

(58) Field of Classification Search
CPC ...... A61M 39/1011; A61M 2039/1016; A61M 2039/1027; A61M 2039/1033;
(Continued)

(56) References Cited

U.S. PATENT DOCUMENTS

| 4,886,061 A | 12/1989 | Fischell et al. |
| 4,926,858 A | 5/1990 | Gifford, III et al. |

(Continued)

FOREIGN PATENT DOCUMENTS

| CN | 109199533 A | 1/2019 |
| DE | 19811364 A1 | 9/1999 |

(Continued)

OTHER PUBLICATIONS

International Search Report dated Jan. 30, 2020 for PCT/US2019/061137.

*Primary Examiner* — Jocelin C Tanner
(74) *Attorney, Agent, or Firm* — Nasr Patent Law LLC; Faisal K. Abou-Nasr

(57) ABSTRACT

In embodiments of an obstruction removal device, system, and/or method, an expandable member is configured to be slidably coupled to a guide wire. The expandable member is configured to surround at least a portion of an obstruction captured by a stentriever as the expandable member transitions from the expanded state to the contracted state, i.e., when the guide wire is removed from a vasculature to remove the stentriever and the obstruction from the vasculature. A first locking member is located at a base of the expandable member. The first locking member is configured to engage a second locking member that is located on the guide wire, the stentriever, or an inner surface of a guide catheter, thereby coupling the expandable member to the guide wire, the stentriever, or the inner surface of the guide catheter when the expandable member is deployed within the vasculature.

11 Claims, 14 Drawing Sheets

(51) Int. Cl.
*A61B 17/22* (2006.01)
*A61B 17/00* (2006.01)

(52) U.S. Cl.
CPC .............. *A61B 2017/00358* (2013.01); *A61B 2017/00778* (2013.01); *A61B 2017/22034* (2013.01); *A61B 2017/22049* (2013.01)

(58) Field of Classification Search
CPC ... A61M 2039/1038; A61B 2017/2212; A61B 2017/22049; A61B 2017/22034; A61B 2017/00778; A61B 2017/00358; A61B 2017/2215; A61B 2017/2905; A61B 2017/2946; A61B 2017/22035; A61B 2017/2217; A61B 17/221; A61B 17/22031; A61B 17/29
See application file for complete search history.

(56) References Cited

U.S. PATENT DOCUMENTS

| | | | |
|---|---|---|---|
| 5,772,674 A | 6/1998 | Nakhjavan | |
| 5,910,154 A * | 6/1999 | Tsugita | A61F 2/013 606/200 |
| 6,001,118 A * | 12/1999 | Daniel | A61B 17/22031 606/200 |
| 6,210,370 B1 | 4/2001 | Chi-Sing et al. | |
| 6,277,139 B1 * | 8/2001 | Levinson | A61B 17/221 606/200 |
| 6,309,399 B1 | 10/2001 | Barbut et al. | |
| 6,796,976 B1 * | 9/2004 | Chin | A61M 25/01 604/164.07 |
| 6,800,085 B2 | 10/2004 | Selmon et al. | |
| 7,041,117 B2 | 5/2006 | Suon et al. | |
| 8,608,754 B2 | 12/2013 | Wensel et al. | |
| 8,777,976 B2 | 7/2014 | Brady et al. | |
| 8,801,748 B2 | 8/2014 | Martin | |
| 8,986,241 B2 | 3/2015 | Evans et al. | |
| 9,125,728 B2 | 9/2015 | Angel et al. | |
| 9,149,609 B2 | 10/2015 | Ansel et al. | |
| 9,597,171 B2 | 3/2017 | Shrivastava et al. | |
| 9,833,252 B2 | 12/2017 | Sepetka et al. | |
| 9,943,323 B2 | 4/2018 | Martin et al. | |
| 9,987,028 B2 | 6/2018 | Lowinger et al. | |
| 10,070,878 B2 | 9/2018 | Ma | |
| 10,076,347 B2 | 9/2018 | Sepetka et al. | |
| 10,143,482 B2 | 12/2018 | Nguyen et al. | |
| 10,172,633 B2 | 1/2019 | Martin et al. | |
| 10,231,751 B2 | 3/2019 | Sos | |
| 10,271,863 B2 | 4/2019 | Marks et al. | |
| 10,314,600 B2 | 6/2019 | Morsi | |
| 10,383,644 B2 | 8/2019 | Molaei et al. | |
| 2002/0072764 A1 * | 6/2002 | Sepetka | A61M 25/0082 606/200 |
| 2005/0251197 A1 * | 11/2005 | Hensley | 606/200 |
| 2006/0229658 A1 * | 10/2006 | Stivland | A61F 2/011 606/200 |
| 2007/0191866 A1 | 8/2007 | Palmer et al. | |
| 2009/0198269 A1 | 8/2009 | Hannes et al. | |
| 2010/0131000 A1 | 5/2010 | DeMello et al. | |
| 2010/0249815 A1 | 9/2010 | Jantzen et al. | |
| 2011/0060359 A1 | 3/2011 | Hannes et al. | |
| 2013/0006284 A1 | 1/2013 | Aggerholm et al. | |
| 2014/0257245 A1 | 9/2014 | Rosenbluth et al. | |
| 2015/0265299 A1 | 9/2015 | Cooper et al. | |
| 2016/0361077 A1 | 12/2016 | Marks et al. | |
| 2017/0143359 A1 * | 5/2017 | Nguyen | A61F 2/013 |
| 2017/0325830 A1 | 11/2017 | Martin et al. | |
| 2018/0008393 A1 | 1/2018 | Volobuyev et al. | |
| 2018/0036028 A1 * | 2/2018 | Krolik | A61B 17/221 |
| 2018/0206865 A1 * | 7/2018 | Martin | A61B 17/221 |
| 2018/0221037 A1 * | 8/2018 | Martin | A61F 2/01 |
| 2018/0256177 A1 | 9/2018 | Cooper et al. | |
| 2018/0271537 A1 * | 9/2018 | Bosaeus | A61B 17/12172 |
| 2018/0325647 A1 | 11/2018 | Hauser | |
| 2019/0000492 A1 | 1/2019 | Casey et al. | |
| 2019/0014121 A1 | 1/2019 | Martin | |
| 2019/0125396 A1 | 5/2019 | Avneri et al. | |
| 2019/0239905 A1 | 8/2019 | Olson et al. | |
| 2019/0298396 A1 | 10/2019 | Gamba et al. | |
| 2019/0314606 A1 | 10/2019 | di Palma et al. | |

FOREIGN PATENT DOCUMENTS

| | | |
|---|---|---|
| EP | 1237489 A1 | 9/2002 |
| EP | 2470088 B1 | 6/2017 |
| EP | 3505091 A1 | 7/2019 |
| JP | 2018134534 A | 8/2018 |
| WO | 2014002087 A1 | 1/2014 |
| WO | 2018043279 A1 | 3/2018 |
| WO | 2018043281 A1 | 3/2018 |
| WO | 2018118706 A1 | 6/2018 |
| WO | 2018160935 A1 | 9/2018 |
| WO | 2019051425 A1 | 3/2019 |

* cited by examiner

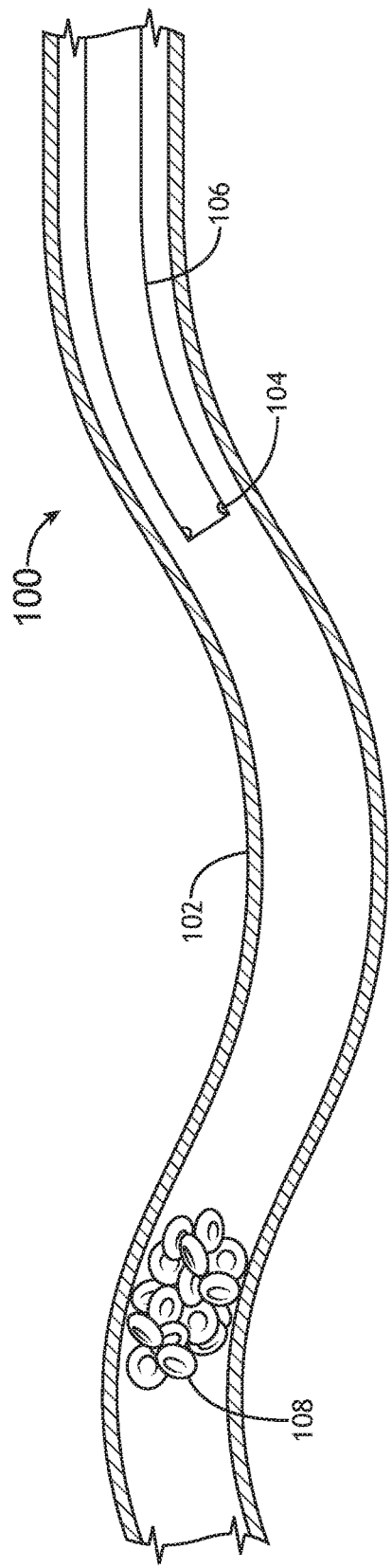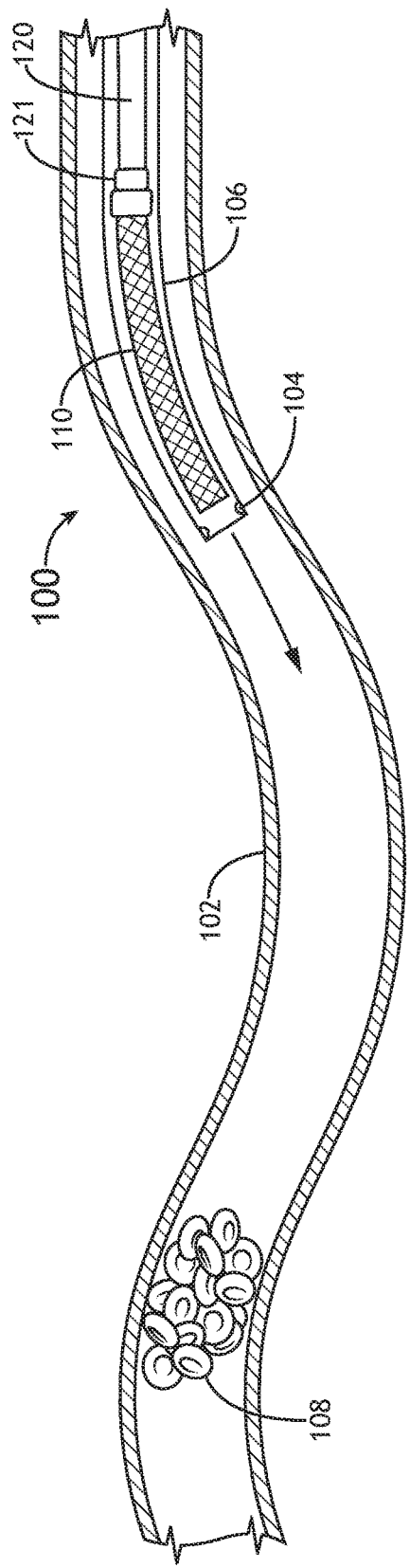

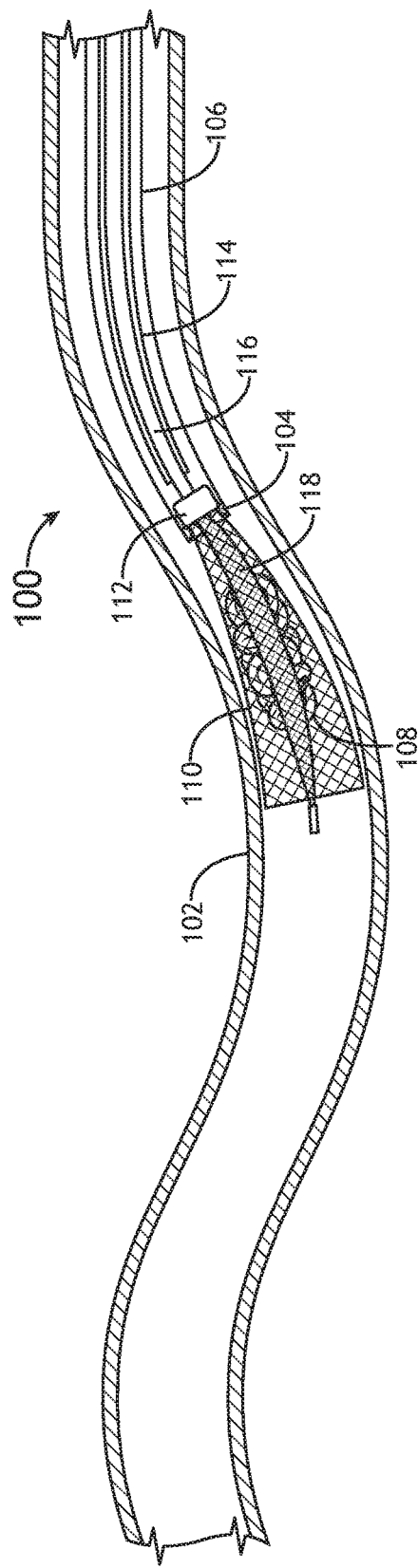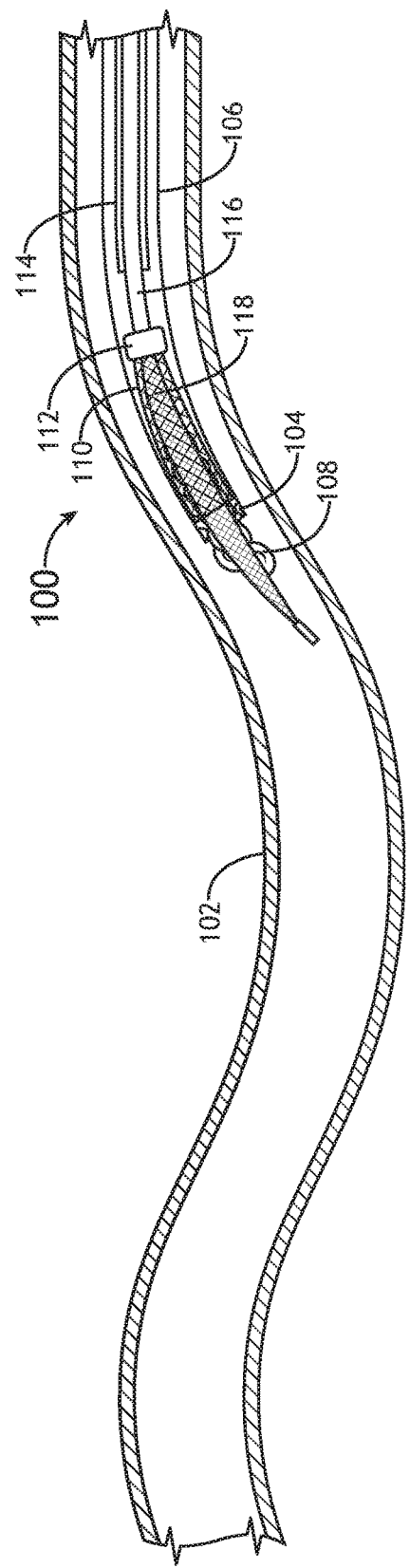

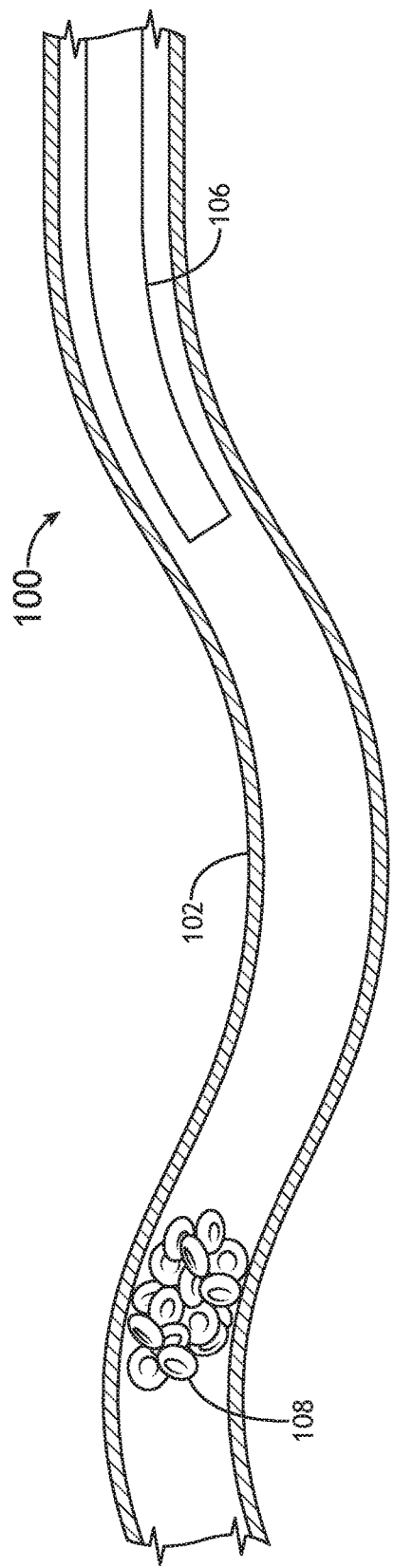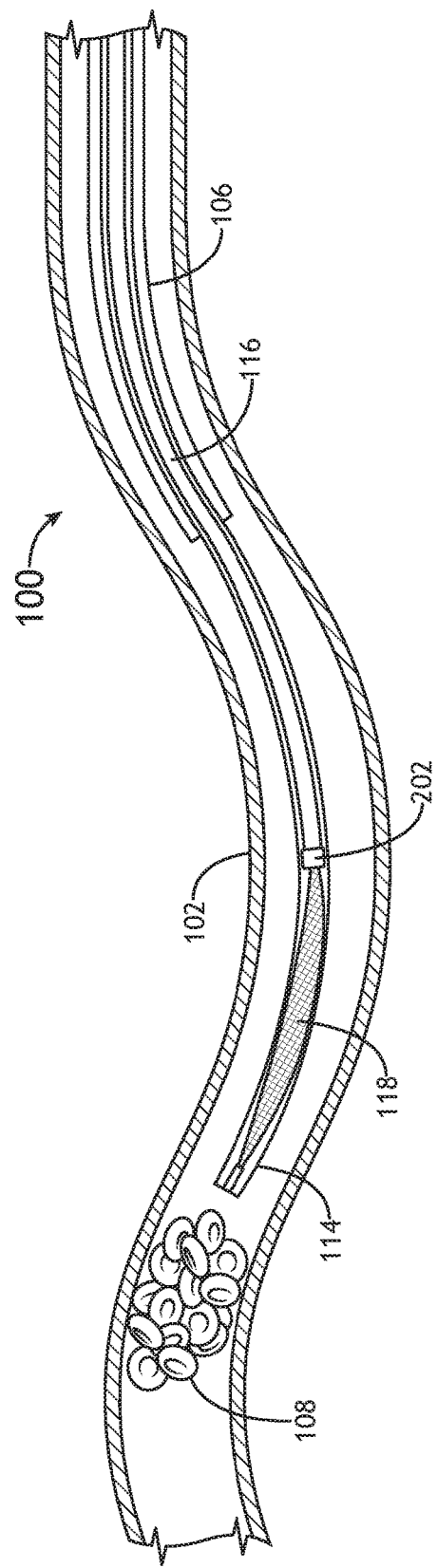

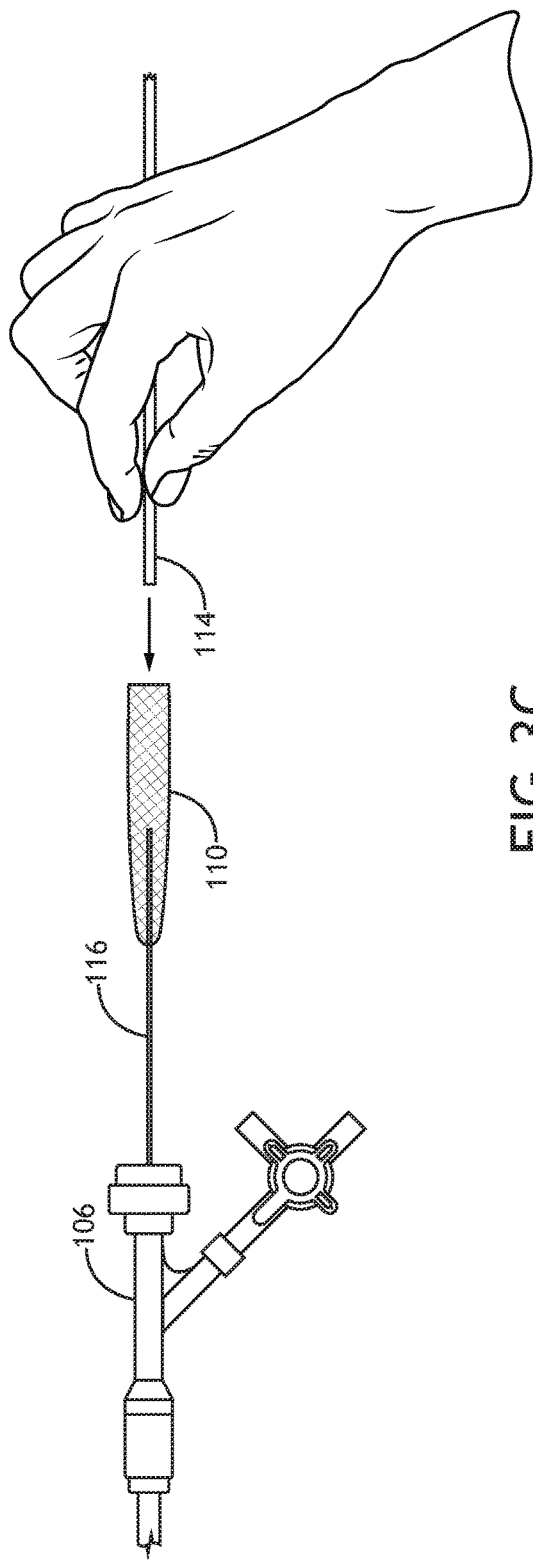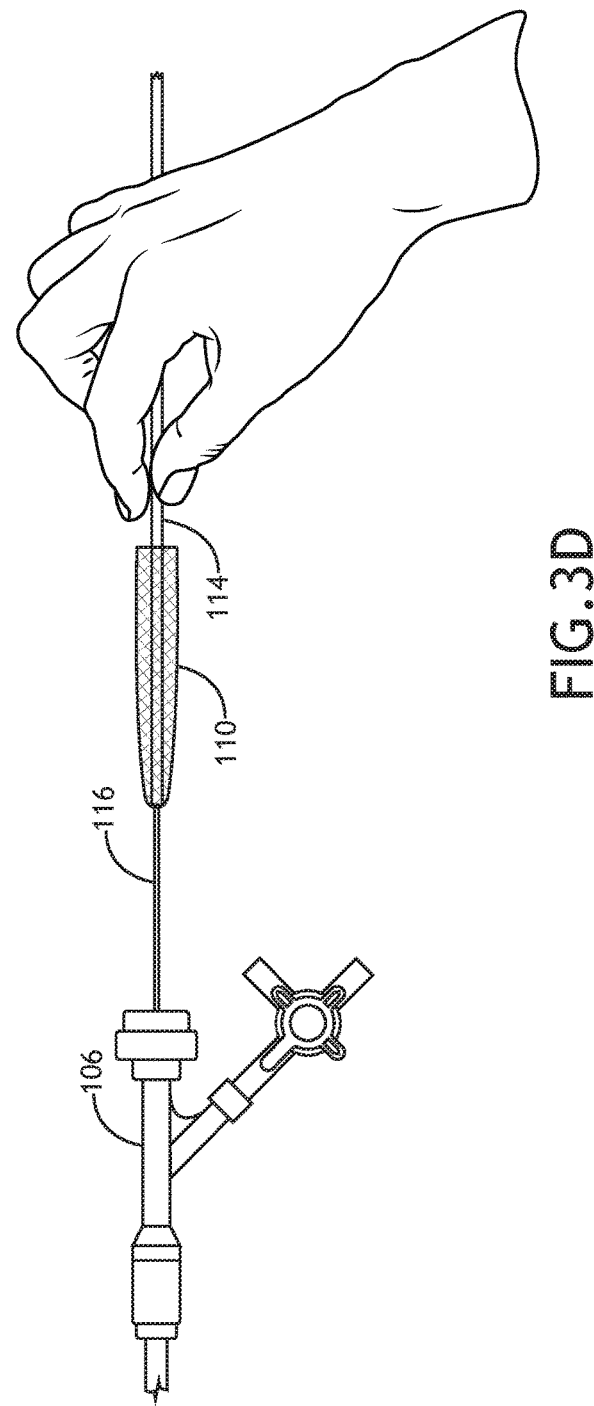
FIG. 3C
FIG. 3D

APPARATUS, SYSTEM, AND METHOD FOR VASCULATURE OBSTRUCTION REMOVAL

CROSS-REFERENCE TO RELATED APPLICATION

The present application claims the benefit under 35 U.S.C. § 119(e) of U.S. Provisional Application Ser. No. 62/767,852, filed Nov. 15, 2018, and titled "APPARATUS, SYSTEM, AND METHOD FOR VASCULATURE OBSTRUCTION REMOVAL," which is incorporated herein by reference in its entirety.

TECHNICAL FIELD

The present invention generally relates to medical devices, and, more particularly, to medical devices for removing vascular obstructions.

BACKGROUND

Obstruction removal systems/devices may operate by lodging the obstruction in a component of the removal system. In some cases, the obstruction may dislodge. Dislodgement of the obstruction substantially increases the risk for potential complications, such as stroke or heart attack. Thus, it is desirable to secure the obstruction safely for removal from the body.

SUMMARY

An obstruction removal system is disclosed. In one or more embodiments, the obstruction removal system includes a guide catheter configured to be inserted within a vasculature and a guide wire having a distal end configured to be inserted within the guide catheter and disposed proximate to an obstruction in the vasculature. A stentriever is disposed at a distal end of the guide wire, and the stentriever is configured to engage the obstruction in the vasculature. An expandable member is slidably coupled to the guide wire, and the expandable member is configured to transition between a contracted state and an expanded state. The expandable member is configured to surround at least one portion of the stentriever and the obstruction as the expandable member transitions from the expanded state to the contracted state, i.e., when the guide wire is removed from the vasculature to remove the stentriever and the obstruction from the vasculature. A first locking member is located at a base of the expandable member. The first locking member is configured to engage a second locking member that is located on the guide wire, the stentriever, or an inner surface of the guide catheter, thereby coupling the expandable member to the guide wire, the stentriever, or the inner surface of the guide catheter when the expandable member is deployed within the vasculature.

More generally, an obstruction removal device is disclosed. In one or more embodiments, the obstruction removal device includes an expandable member configured to be slidably coupled to a guide wire. The expandable member is configured to transition between a contracted state and an expanded state. The expandable member is further configured to surround at least one portion of a stentriever and an obstruction as the expandable member transitions from the expanded state to the contracted state, i.e., when the guide wire is removed from a vasculature to remove the stentriever and the obstruction from the vasculature. A first locking member is located at a base of the expandable member. The first locking member is configured to engage a second locking member that is located on the guide wire, the stentriever, or an inner surface of a guide catheter, thereby coupling the expandable member to the guide wire, the stentriever, or the inner surface of the guide catheter when the expandable member is deployed within the vasculature.

A method for removing an obstruction from a vasculature is also disclosed. In one or more embodiments, the method includes the steps of: inserting a guide catheter within a vasculature; extending a guide wire through the guide catheter so that a distal end of the guide wire is disposed proximate to the obstruction in the vasculature; engaging at least one portion of the obstruction in the vasculature with a stentriever disposed at the distal end of the guide wire; sliding an expandable member along the guide wire until a first locking member at a base of the expandable member engages a second locking member on the guide wire, the stentriever, or an inner surface of the guide catheter, thereby coupling the expandable member to the guide wire, the stentriever, or the inner surface of the guide catheter, the expandable member being configured to transition between a contracted state and an expanded state; and removing the guide wire from the vasculature to remove the stentriever and the obstruction from the vasculature, wherein the expandable member is configured to surround at least one portion of the stentriever and the obstruction as the expandable member transitions from the expanded state to the contracted state when the guide wire is removed from the vasculature to remove the stentriever and the obstruction from the vasculature.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 1A illustrates a cross-sectional side view of a guide catheter of an obstruction removal system deployed within a vasculature, in accordance with one or more embodiments of the present disclosure.

FIG. 1B illustrates a cross-sectional side view of an expandable member of the obstruction removal system deployed through the guide catheter, in accordance with one or more embodiments of the present disclosure.

FIG. 1I illustrates a cross-sectional side view of the stentriever of the obstruction removal system being pulled back through the guide catheter to remove the obstruction from the vasculature, in accordance with one or more embodiments of the present disclosure.

FIG. 1J illustrates a cross-sectional side view of the expandable member of the obstruction removal system being pulled back through the guide catheter with the stentriever, wherein the expandable member transitions to a contracted state and surrounds at least a portion of the obstruction as the expandable member is pulled into the guide catheter, in accordance with one or more embodiments of the present disclosure.

FIG. 2A illustrates a cross-sectional side view of a guide catheter of an obstruction removal system deployed within a vasculature, in accordance with one or more embodiments of the present disclosure.

FIG. 2B illustrates a cross-sectional side view of a stentriever of the obstruction removal system deployed through the guide catheter, wherein the stentriever is attached to a guide wire that is fed through the guide catheter using a microcatheter, in accordance with one or more embodiments of the present disclosure.

FIG. 3C illustrates the expandable member loaded onto the guide wire for deployment through the guide catheter, wherein the expandable member is pushed along the guide wire by a microcatheter, in accordance with one or more embodiments of the present disclosure.

FIG. 3D illustrates the expandable member loaded onto the guide wire for deployment through the guide catheter, wherein the expandable member is pushed along the guide wire by a microcatheter, in accordance with one or more embodiments of the present disclosure.

DETAILED DESCRIPTION

Figure 1C:
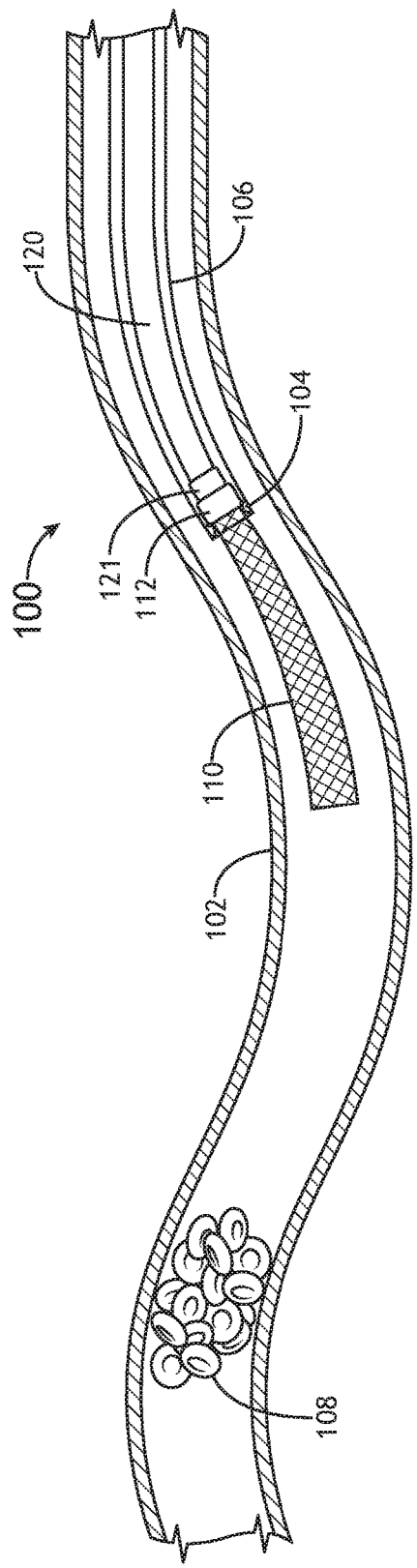
FIG. 1C illustrates a cross-sectional side view of the expandable member of the obstruction removal system deployed through the guide catheter until a base member of the expandable member reaches one or more guide stops, wherein the expandable member is pushed through the guide catheter by a delivery wire/tube, in accordance with one or more embodiments of the present disclosure.

Reference will now be made in detail to the subject matter disclosed, which is illustrated in the accompanying drawings. Referring generally to FIGS. 1A through 9, an obstruction removal system is described, in particular, an obstruction removal system configured to selectively deploy an expandable member in a vasculature to reduce the risks associated with removal of an obstruction. The expandable member may be used to prevent an obstruction from dislodging from a stentriever and passing to a potentially more dangerous area (e.g. causing a total blockage, blocking a portion of a vital vasculature, etc.). In this regard, a physician may determine whether an obstruction is prone to risk and selectively deploy the expandable member. Furthermore, the physician may deploy the expandable member at various locations away from the obstruction (e.g., clot), as needed.

In embodiments, the obstruction removal system comprises a guide catheter, a guide wire, an expandable member, and first and second locking members. The first locking member may be attached to the base of the expandable member, such that translation of the expandable member results in translation of the first locking member. The first locking member may be further configured to engage the second locking member. In this regard, the expandable member may be fixed to the second locking member by the first locking member.

The expandable member may be inserted within the guide catheter by a guide wire and/or microcatheter and disposed proximate to an obstruction in the vasculature. The guide wire and/or microcatheter may be further configured to engage the first locking member to the second locking member.

The expandable member may be configured to transition between one or more positions, such as, a contracted state and an expanded state. The expanded state may allow the expandable member to surround a portion of at least one of the stentriever and/or the obstruction. The contracted state may be suitable for insertion and removal of the expandable member through the guide catheter and/or a microcatheter. In this regard, when the expandable member is in the collapsed/contracted state after surrounding at least a portion of the stentriever and/or the obstruction, the expandable member, and the stentriever may be withdrawn through the guide catheter and/or the microcatheter.

Benefits for surrounding a portion of the stentriever or the obstruction in an expandable member may include, but are not limited to, smaller cross-sectional area, reduced friction on a vessel wall, reduced likelihood of catching on an opening of the guide catheter, reduced likelihood of catching on an opening of a microcatheter, and reduced likelihood of obstruction dislodgement.

The expandable member is configured to transition between the one or more positions (e.g. contracted state and collapsed position) in any suitable way, including, but not limited to, internal stresses, friction, material properties, wires attached to the expandable member, hooks to grab on to/make contact with a portion of a vessel wall, or a mating surface between the first locking member and the second locking member.

In some embodiments, the first locking member may be configured to disengage from the second locking member when the delivery system is removed from the vasculature. In this regard, the disengagement of the first locking member from the second locking member may be used to remove the stentriever and obstruction from the vasculature. The ability to disengage the first and second locking member may allow reuse of the guide wire, the stentriever, the expandable member, the guide catheter, and/or the microcatheter. The first and second locking member may engage by any suitable means, including but not limited to, guide stops, snap-fit connectors, cooperatively threaded connectors, magnetic connectors, or the like.

In embodiments, the second locking member may be attached in several locations, including, but not limited to, the stentriever, the guide wire, or an inner surface of the guide catheter. In this regard, after the first and second locking member engage, the first and second locking member will be fixed relative to the stentriever, the guide wire, or the guide catheter.

It is to be understood that the first and second locking member may be configured to engage at various points during the removal of the obstruction from the vasculature. For example, the first and second locking member may engage before or after the stentriever engages the obstruction. The order of engagement listed is not intended to be limiting.

FIGS. 1A through 1K illustrate one or more embodiments of an obstruction removal system 100. As shown in FIG. 1A, the obstruction removal system 100 includes a guide catheter 106 configured to be inserted through a vasculature to a position proximate to an obstruction 108. The obstruction removal system 100 may include guide stops 104 attached (e.g., mounted) to or formed on an inner surface of the guide catheter 106, at or near a distal end of the guide catheter (e.g. near an opening of the guide catheter).

As shown in FIG. 1B, the obstruction removal system 100 further includes an expandable member 110. In a contracted state, the expandable member 110 is configured to be inserted through the guide catheter and out of a distal opening of the guide catheter 106. When the expandable member 110 is in the contracted state, the expandable member may fit through the guide stops 104.

Figure 1D:
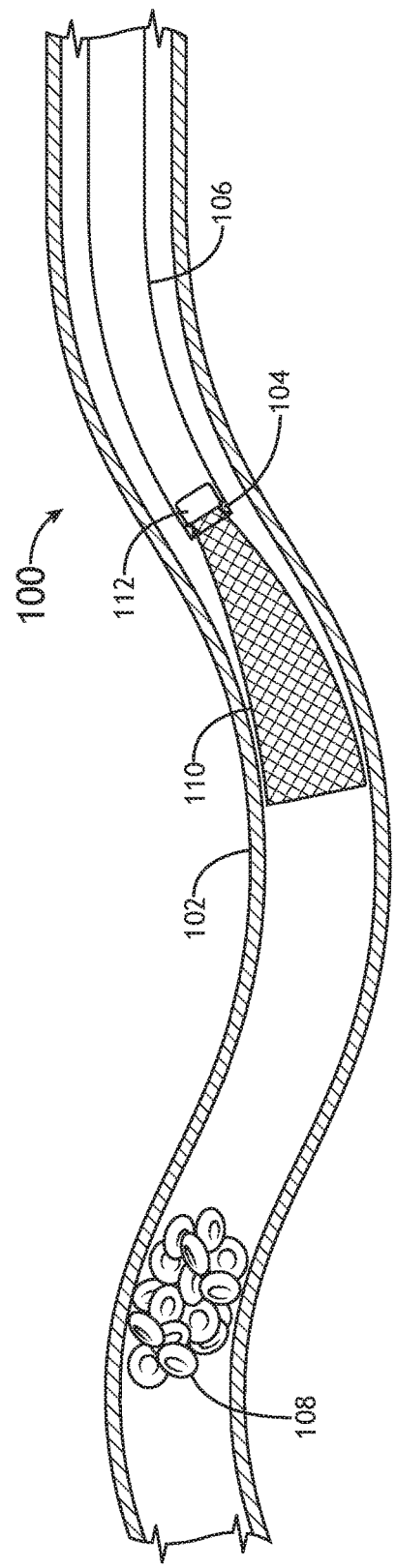
FIG. 1D illustrates a cross-sectional side view of the expandable member of the obstruction removal system deployed through the guide catheter until a base member of the expandable member reaches one or more guide stops, wherein the delivery wire/tube has been removed, in accordance with one or more embodiments of the present disclosure.

FIG. 1C further illustrates the expandable member 110 deployed out of the distal opening of the guide catheter 106, where a base member 112 attached to the expandable member 110 is pushed up against, mated with, or otherwise engaged with the guide stops 104. A delivery tool 120 (e.g., a delivery wire or delivery tube) may be used to push the expandable member 110 through the guide catheter 106. In some embodiments, the delivery tool 120 may include an end-mounted support member 121 configured to support the expandable member 110 as the expandable member 110 is pushed through the guide catheter 106. FIG. 1D further illustrates the expandable member 110 transitioned to an expanded state. The delivery tool 120 can then be removed from the vasculature.

It is to be understood that the use of guide stops 104 on an inner portion of a guide catheter 106 may be suitable to allow a physician to selectively position the expandable member 110 at an appropriate distance from an obstruction 108 by translating some portion of the guide catheter 106 and/or the delivery tool 120. When positioning the guide catheter 106 and the expandable member 110, the physician may account for such things as vasculature geometry, obstruction size, blood pressure, blood flow direction, or vasculature tissue strength. For example, it may be undesirable to deploy the expandable member 110 near the obstruction location (e.g. due to a complex vasculature structure) but may still be desirable to use the expandable member 110 (e.g. to reduce likelihood of separation of the obstruction 108 from a stentriever). In this example, the expandable member 110 may be deployed away from the obstruction 108 and still retain the benefit of reducing complications due to obstruction dislodgement.

Figure 1E:
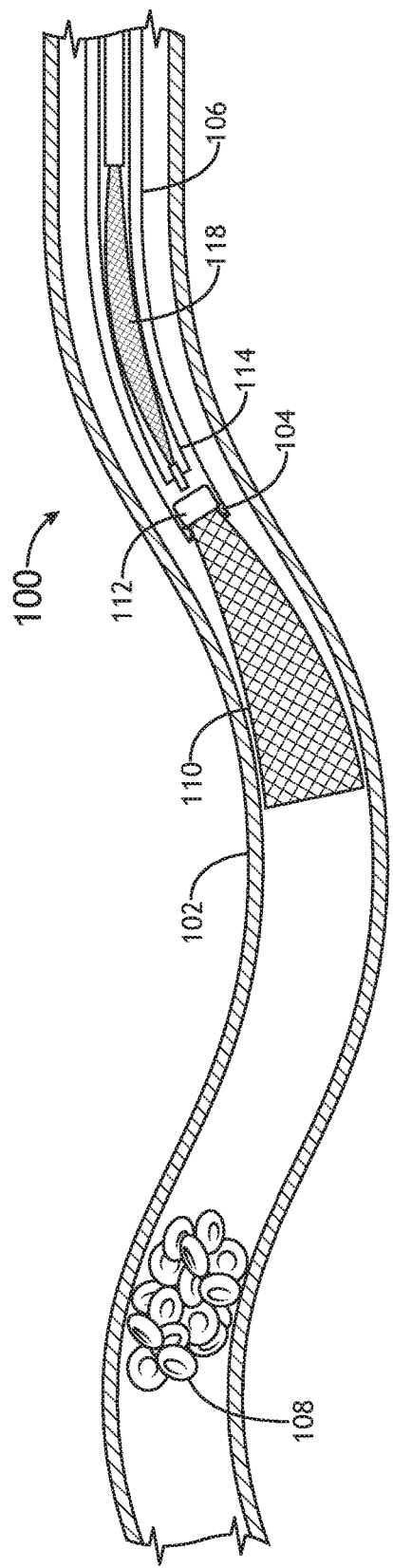
FIG. 1E illustrates a cross-sectional side view of a stentriever of the obstruction removal system deployed through the guide catheter, wherein the stentriever is attached to a guide wire that is fed through the guide catheter using a microcatheter, in accordance with one or more embodiments of the present disclosure.

Referring now to FIG. 1E, the obstruction removal system 100 may further include a stentriever 118 configured to be inserted through the guide catheter 106. For example, the stentriever 118 may be coupled or formed on/near a distal end of a guide wire 116 configured to be inserted through the guide catheter 106. In embodiments, the stentriever 118 may be housed within a microcatheter 114 (e.g., any suitable microcatheter or tube). The microcatheter 114 may be used to contain the stentriever 118 and keep the stentriever 118 from expanding within the guide catheter 106. This may provide one or more advantages, such as, but not limited to, reducing friction between the stentriever 118 and the guide catheter 106, permitting the stentriever 118 to be inserted through the base member 112 and/or the distal opening of the guide catheter 106, and preventing the stentriever 118 from prematurely engaging with the expandable member 110.

Figure 1F:
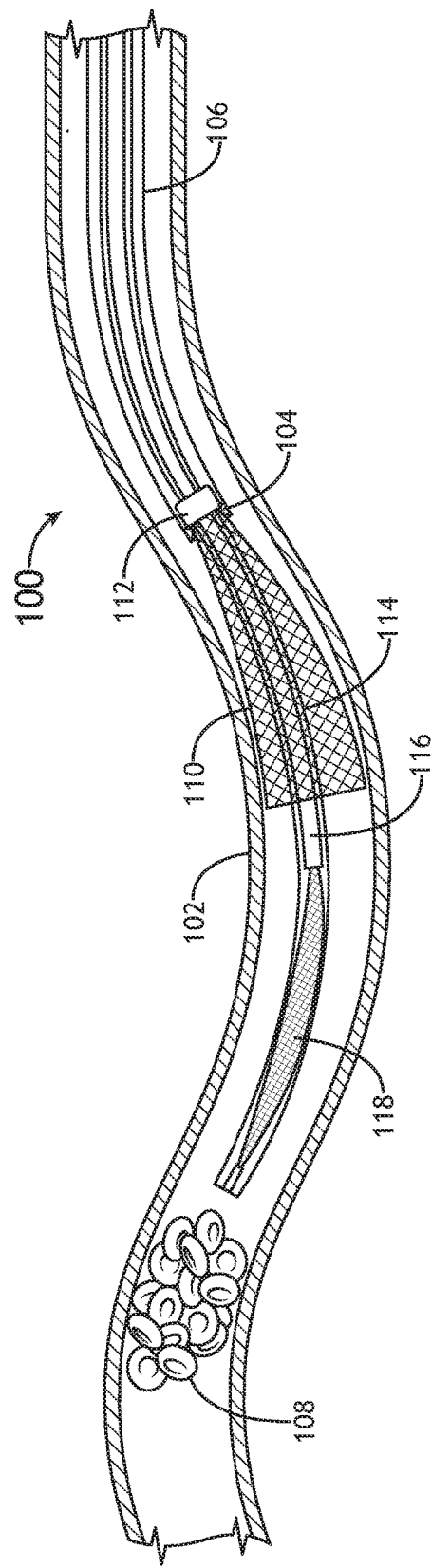
FIG. 1F illustrates a cross-sectional side view of the stentriever of the obstruction removal system deployed through the guide catheter, wherein the stentriever attached to the guide wire is fed through the guide catheter and the expandable member using the microcatheter, in accordance with one or more embodiments of the present disclosure.

FIG. 1F illustrates the stentriever 118, microcatheter 114, and guide wire 116 inserted through the base member 112, the expandable member 110, and the distal opening of the guide catheter 106. The stentriever 118 is attached to the guide wire 116, so that translation of the guide wire 116 results in translation of the stentriever 118.

Figure 1G:
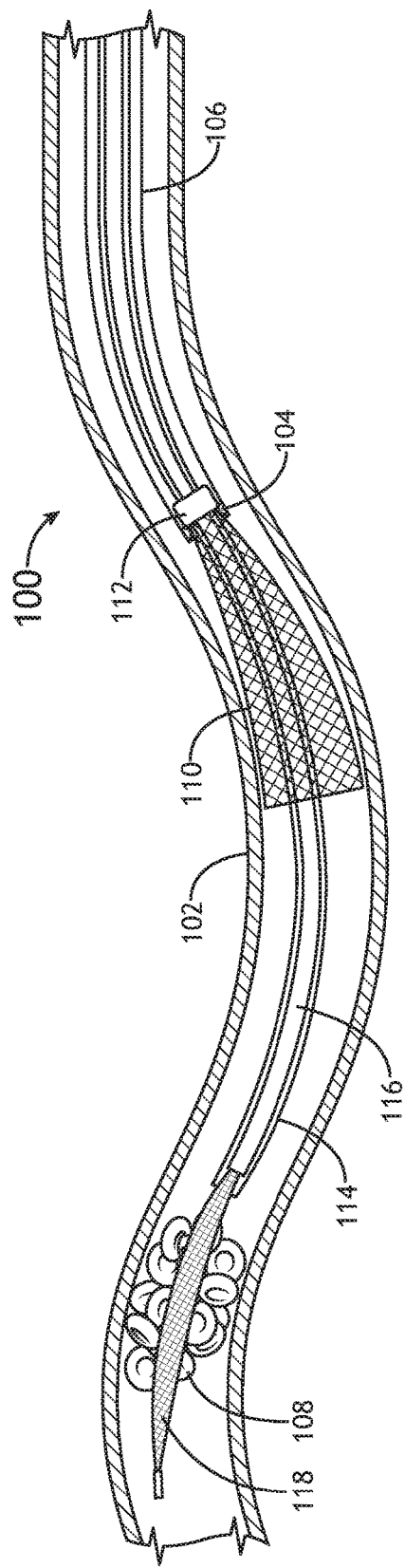
FIG. 1G illustrates a cross-sectional side view of the stentriever of the obstruction removal system deployed within the vasculature, wherein the microcatheter is pulled back to unsheathe the stentriever so that the stentriever can engage an obstruction in the vasculature, in accordance with one or more embodiments of the present disclosure.

FIG. 1G illustrates the stentriever 118 after the stentriever 118 has been deployed out of a distal end of the microcatheter 114 and at least partially engaging the obstruction 108. It is to be understood that there may be one or more methods for engaging the obstruction 108 with the stentriever 118. For example, the microcatheter 114 may be deployed through/alongside of the obstruction 108, with the stentriever 118 contained within the microcatheter 114. The microcatheter 114 may then be withdrawn, permitting the stentriever 118 to expand and engage the obstruction 108.

Figure 1H:
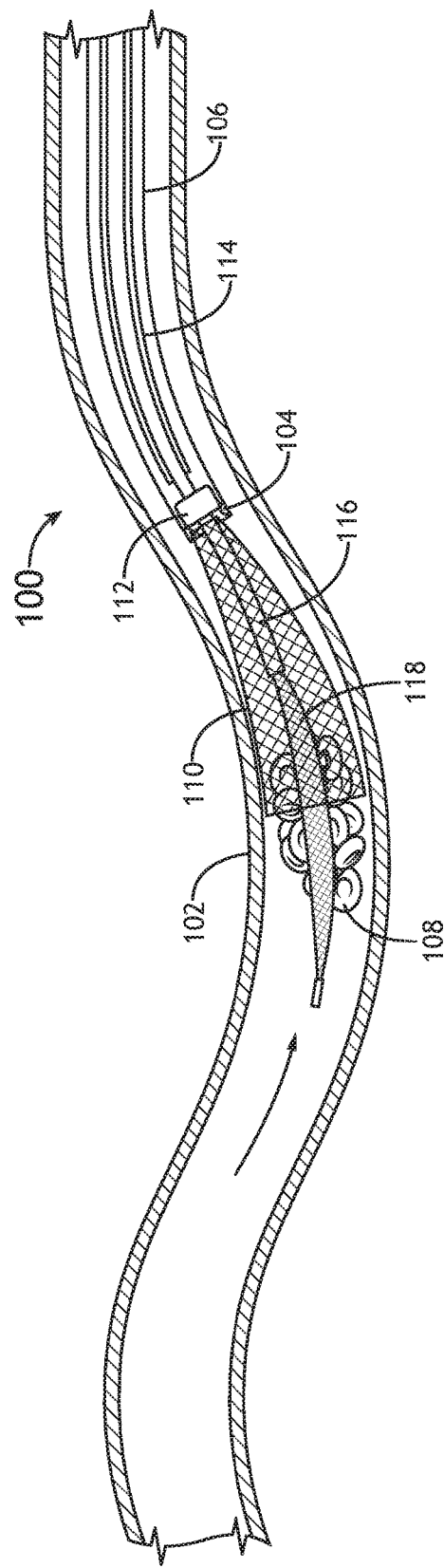
FIG. 1H illustrates a cross-sectional side view of the stentriever of the obstruction removal system being pulled back through the guide catheter to remove the obstruction from the vasculature, in accordance with one or more embodiments of the present disclosure.

FIGS. 1H and 1I illustrate the guide wire 116 withdrawing the stentriever 118 (and the obstruction 108) towards the expandable member 110. The expandable member 110 may be configured in an expanded state, such that the expandable member 110 may surround at least a portion of the obstruction 108 and/or stentriever 118 as the stentriever 118 and the obstruction 108 are pulled into the guide catheter 106. As the guide wire 116 is withdrawn and removed from the vasculature, the expandable member 110 may transition from the expanded state to a contracted/collapsed state, thereby causing the expandable member 110 to at least partially surround and clench the obstruction 108 so that the obstruction 108 can be safely removed from the vasculature.

FIG. 1J illustrates the expandable member 110 withdrawn into the guide catheter 106 in a collapsed position. In some embodiments, the base member 112 may be configured to disengage from the guide stops 104. The guide wire 116 with the stentriever 118, obstruction 108, and expandable member 110 may be withdrawn through the microcatheter 114, as depicted in FIG. 1J. Alternatively, the guide wire 116 with the stentriever 118, obstruction 108, and expandable member 110 may be pulled directly through the guide catheter 106.

Figure 1K:
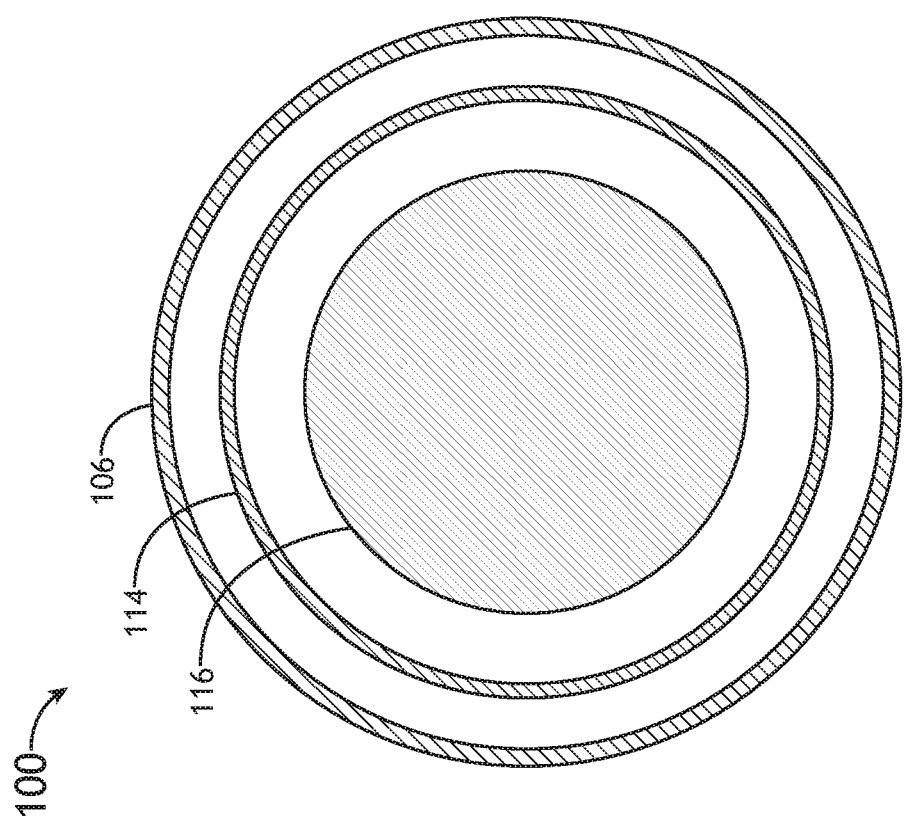
FIG. 1K illustrates a cross-sectional end view of a guide catheter with a microcatheter inserted within the guide catheter and a guide wire inserted within the microcatheter, in accordance with one or more embodiments of the present disclosure.
Figure 1L:
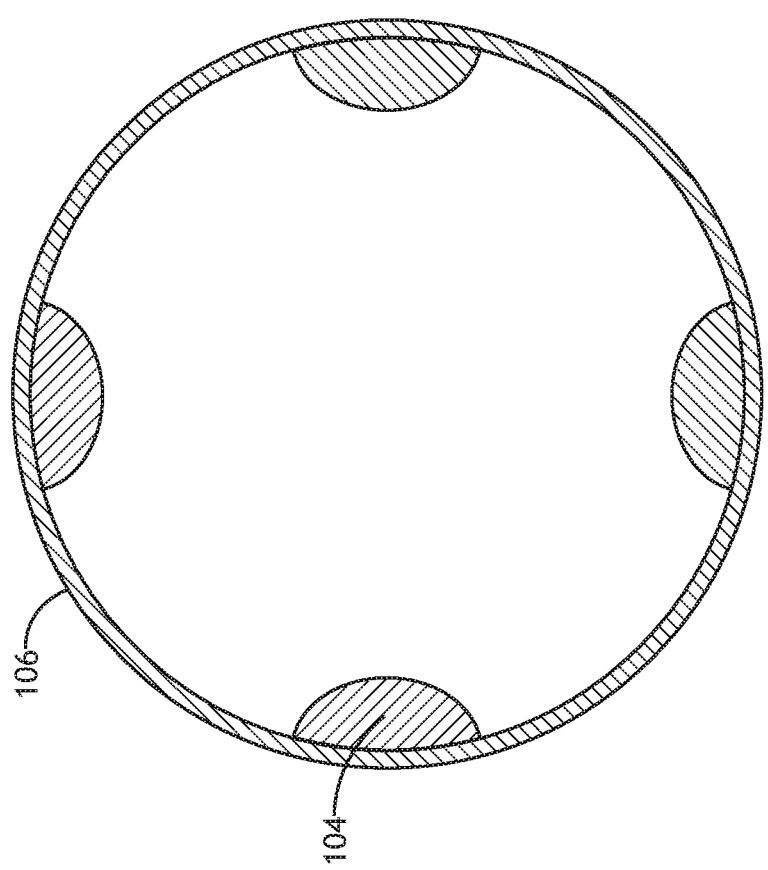
FIG. 1L illustrates a cross-sectional end view of a guide catheter with guide stops attached to an inner surface of the guide catheter, in accordance with one or more embodiments of the present disclosure.

FIG. 1K illustrates a cross-sectional end view of an obstruction removal system, where a guide wire 116 is inserted through a microcatheter 114 and a guide catheter 106, and FIG. 1L illustrates a cross-sectional end view of a guide catheter 106 with guide stops 104 (e.g., one or more protrusions or a ring) attached to an inner surface of the guide catheter 106. The guide stops 104 depicted are not intended to be limiting, but are merely to provide an example of a method/means for engaging a base member. The guide stops 104 may be configured to engage with a base member 112 attached to an expandable member 110 (e.g. by taking up a portion of the cross-sectional area of the guide catheter 106). Additionally, the guide stops may be configured to take up a minimal cross-sectional area of the guide catheter 106, in order to allow injection of radioactive dye. In some embodiments, the guide stops 104 may be further configured to mate with the expandable member 110 to temporarily lock it in place at the distal end of the guide catheter 106.

Figure 2C:
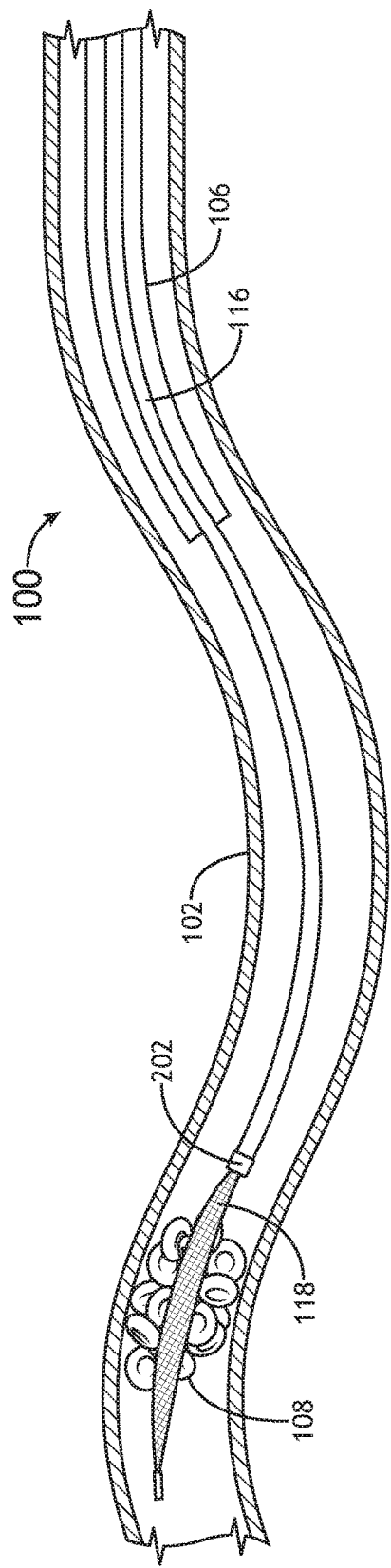
FIG. 2C illustrates a cross-sectional side view of the stentriever of the obstruction removal system deployed within the vasculature, wherein the microcatheter is pulled back to unsheathe the stentriever so that the stentriever can engage an obstruction in the vasculature, in accordance with one or more embodiments of the present disclosure.

FIGS. 2A through 2I illustrate one or more additional embodiments of the obstruction removal system 100. As shown in FIG. 2A, the guide catheter 106 is configured to be inserted through a vasculature to a position proximate to an obstruction 108. FIG. 2B illustrates a stentriever 118 inserted through the guide catheter 106 and out of a distal end of the guide catheter 106, such that the stentriever 118 is in a position proximate to the obstruction 108. In embodiments, the stentriever 118 may be at least partially housed within a microcatheter 114. The stentriever 118 is attached to a distal end of a guide wire 116, such that translation of the guide wire 116 results in translation of the stentriever 118.

Figure 2D:
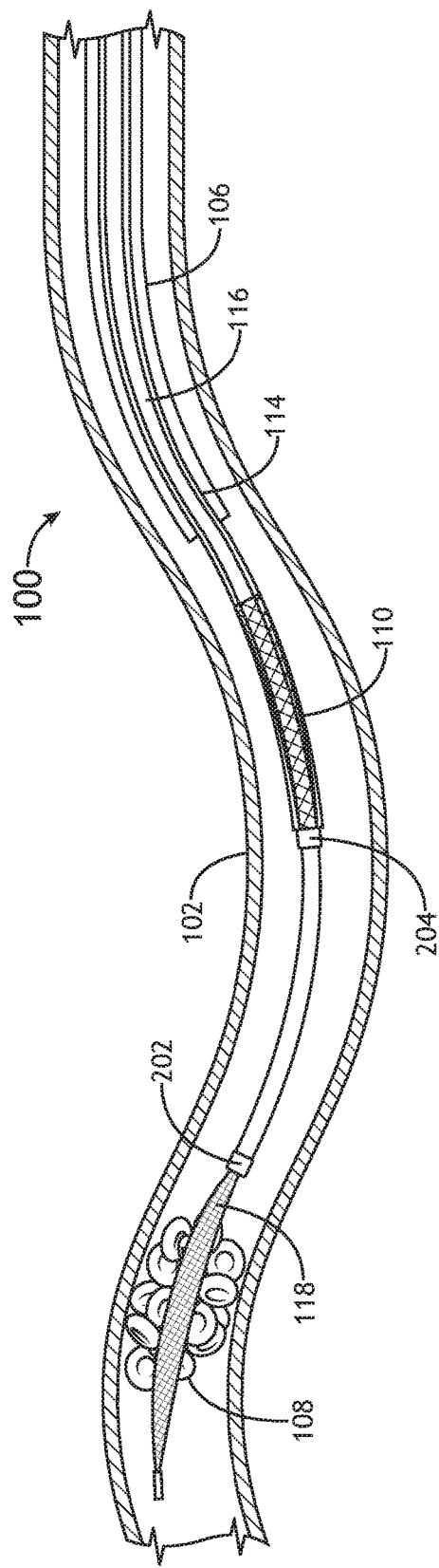
FIG. 2D illustrates a cross-sectional side view of an expandable member of the obstruction removal system deployed through the guide catheter, wherein the expandable member is slidably coupled to the guide wire and pushed through the guide catheter using a microcatheter, in accordance with one or more embodiments of the present disclosure.

FIG. 2C illustrates the stentriever 118 after the stentriever 118 has been deployed out of a distal end of the microcatheter 114 and at least partially engaging the obstruction 108. In FIG. 2C, the microcatheter 114 has been withdrawn through the guide catheter 106. A locking member 202 is located at a position proximate to a base of the stentriever 118, such as, but not limited to, at the base of the stentriever 118, on the guide wire 116 near the base of the stentriever, or some combination of the two. As shown in FIG. 2D, another locking member 204 is located at a base of the expandable member 204.

FIG. 2D illustrates an expandable member 110 being pushed the guide catheter 106 into the vasculature. The expandable member 110 may be slid along the guide wire 116, through the guide catheter 106, by the microcatheter 114. The expandable member 110 is slidably coupled to the guide wire 116 (i.e., configured to slide along the guide wire 116). The microcatheter 114 may be configured to slide the expandable member 110 along the guide wire 116 until locking member 204 engages (e.g., mates with) locking member 202.

The expandable member 110 may be inserted through the guide catheter 106 in a first configuration that permits the expandable member 110 to be housed within the microcatheter 114 while the expandable member is inserted through the guide catheter 106. In this regard, the expandable member 110 may not expand from the first configuration until the microcatheter 114 is withdrawn. Alternatively, the first configuration of the expandable member 110 may permit the expandable member 110 to surround a distal portion of the microcatheter 114. In such cases, the expandable member 110 may expand outwardly when the expandable member 110 is no longer housed within the guide catheter 106.

Figure 2E:
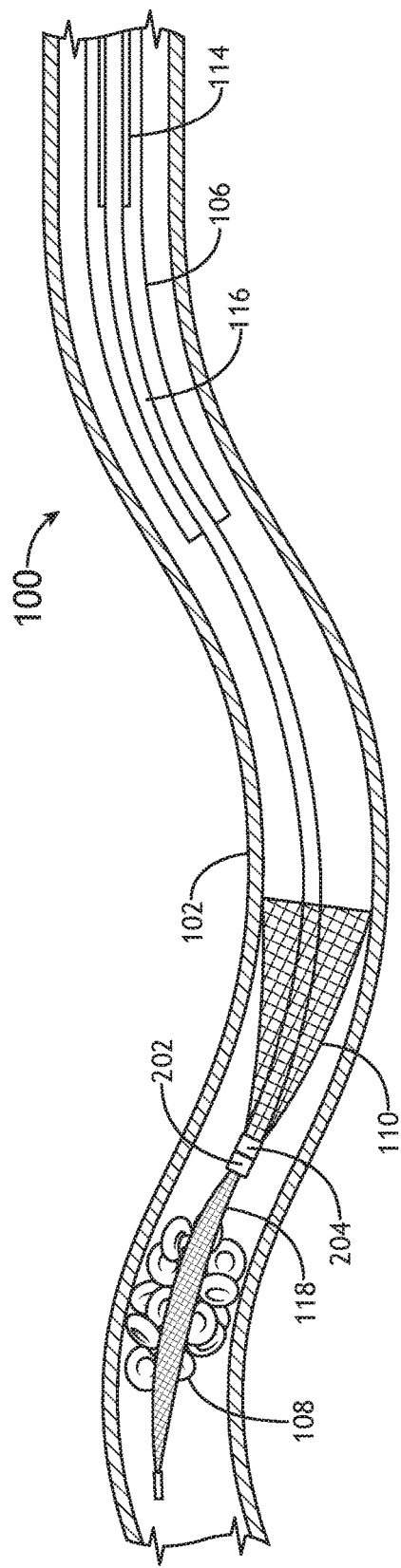
FIG. 2E illustrates a cross-sectional side view of the expandable member of the obstruction removal system deployed within the vasculature after being pushed through the guide catheter, wherein a first locking member at the base of the expandable member is mated with a second locking member on the guide wire and/or stentriever, in accordance with one or more embodiments of the present disclosure.

FIG. 2E illustrates locking member 204 engaged (e.g., mated) with locking member 202 to form a coupling 200 that secures the expandable member 110 to the stentriever 118 and/or a portion of the guide wire near the stentriever 118. In this regard, the stentriever 118 and the expandable member 110 can be moved together by translating the guide wire 116. Additionally, the obstruction 108 can be pulled towards and/or into the guide catheter 106 by withdrawing the guide wire 116.

In FIG. 2E, the microcatheter 114 has been withdrawn into the guide catheter 106. In some embodiments, the microcatheter 114 may remain at a position proximate to locking member 204. In other embodiments, the microcatheter 114 may be withdrawn into the guide catheter 106 after locking member 204 engages locking member 202. In other embodiments, the microcatheter 114 may be withdrawn out of the vasculature.

Figure 2F:
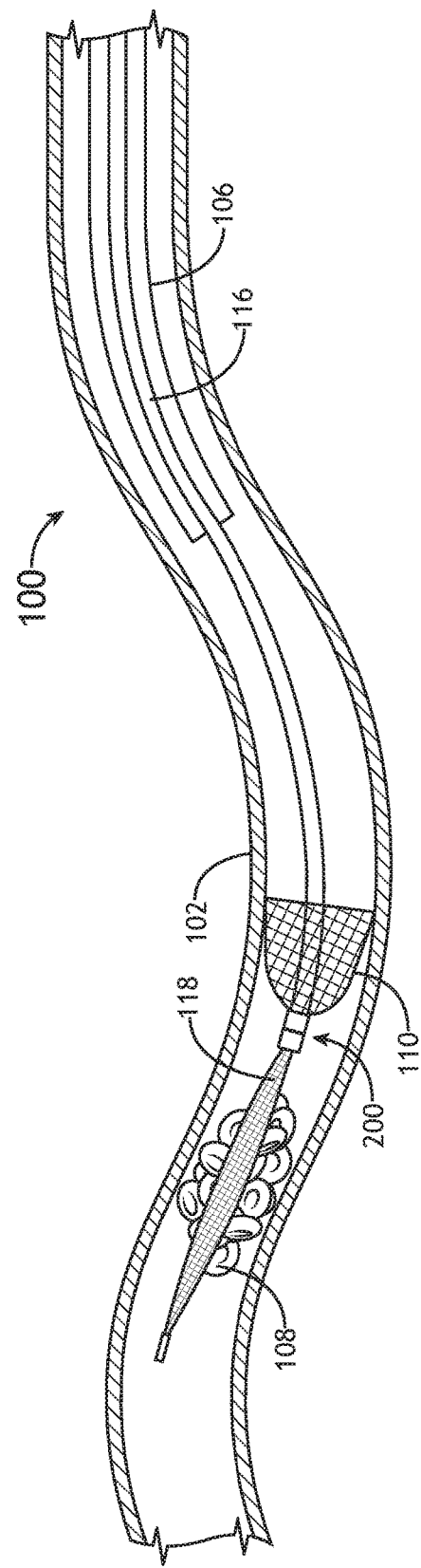
FIG. 2F illustrates a cross-sectional side view of the stentriever of the obstruction removal system being pulled back through the guide catheter to remove the obstruction from the vasculature, wherein the expandable member is inverted as the stentriever is pulled towards and/or into the guide catheter, in accordance with one or more embodiments of the present disclosure.

FIG. 2F illustrates the guide wire 116 withdrawing the stentriever 118, the obstruction 108, and a portion of the expandable member 110 towards a distal opening of the guide catheter 106. As the portion of the expandable member 110 is withdrawn, the expandable member inverts from the first configuration to a second configuration. The inversion of the expandable member may occur due to a frictional force between the expandable member 110 and the vessel wall 102. As the expandable member 110 inverts from the first configuration to the second configuration, an inner portion of the expandable member 110 near the locking member 204 may translate while an outer portion of the expandable member 110 near the vessel wall 102 may remain stationary (or translate at a speed less than the inner portion).

Figure 2G:
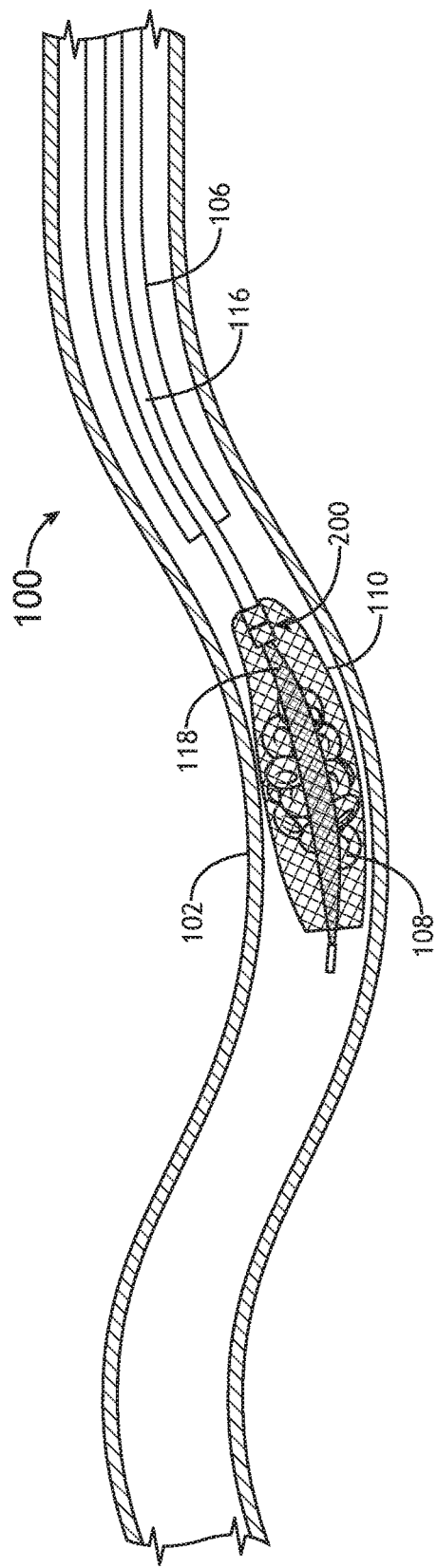
FIG. 2G illustrates a cross-sectional side view of the stentriever of the obstruction removal system being pulled back through the guide catheter to remove the obstruction from the vasculature, wherein the obstruction is at least partially surrounded by the inverted expandable member, in accordance with one or more embodiments of the present disclosure.

After transitioning from the first configuration to the second configuration, the expandable member 110 is configured to surround at least a portion of the obstruction 108 and/or the stentriever 118. FIG. 2G illustrates the expandable member 110 after the expandable member 110 has inverted from the first configuration to the second configuration and surrounded at least a portion of the stentriever 118 and/or the obstruction 108. Surrounding the obstruction 108 with the expandable member 110 may prevent dislodgement of the obstruction 108 during removal.

Figure 2H:
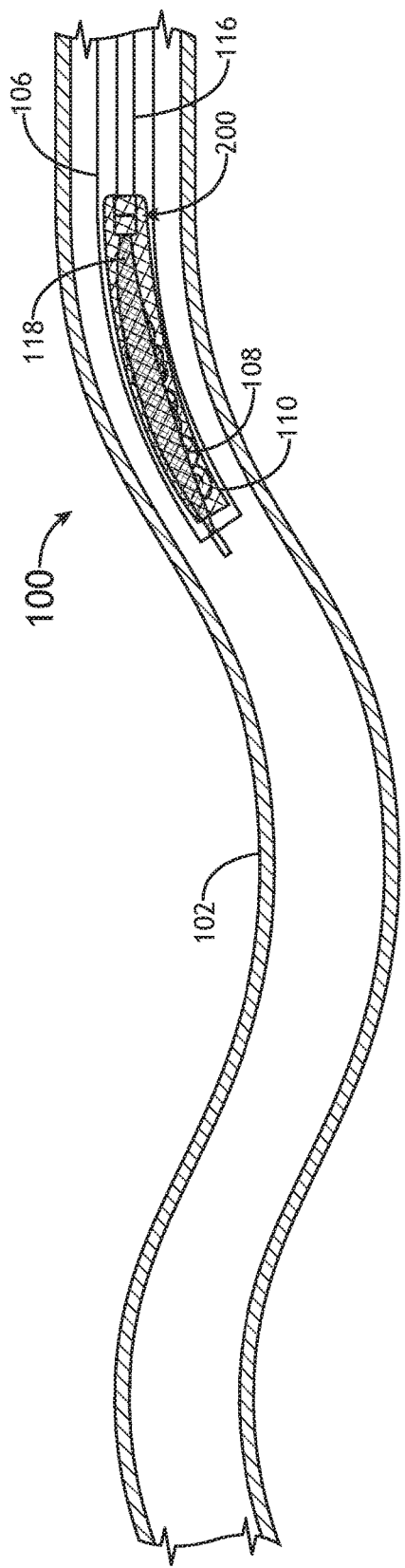
FIG. 2H illustrates a cross-sectional side view of the expandable member of the obstruction removal system being pulled back through the guide catheter with the stentriever, wherein the expandable member transitions to a contracted state and surrounds at least a portion of the obstruction as the expandable member is pulled into the guide catheter, in accordance with one or more embodiments of the present disclosure.

FIG. 2H illustrates the expandable member 110, obstruction 108, and stentriever 118 at least partially withdrawn into the guide catheter 106. In some embodiments, such as the embodiment illustrated in FIG. 2H, the guide wire 116 with the expandable member 110, stentriever 118, and obstruction 108 may be further withdrawn into the microcatheter 114 during removal. Alternatively, the guide wire 116 with the expandable member 110, stentriever 118, and obstruction 108 can be pulled directly through the guide catheter 106.

Figure 2I:
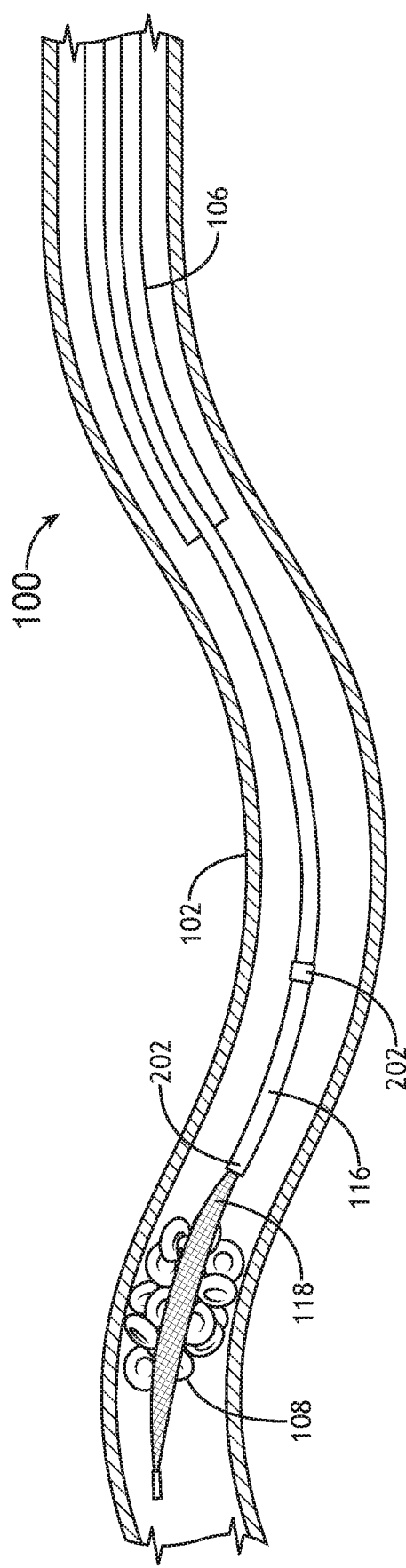
FIG. 2I illustrates a cross-sectional side view of the stentriever of the obstruction removal system deployed within the vasculature, wherein the second locking member is on the guide wire at a distance from the stentriever, in accordance with one or more embodiments of the present disclosure.

FIG. 2I illustrates an embodiment of the obstruction removal system 100, where locking member 202 is located on the guide wire 116 at a distance from the stentriever 118. This configuration may be advantageous in situations where a patient's vasculature structure limits deployment of the expandable member 110, locking member 204, and/or guide catheter 106. In this regard, a physician may have a set of guide wire and stents, where the set of guide wires has receiving members housed at various lengths from the stents (e.g. 25 mm, 50 mm, 75 mm, 100 mm, etc.). The set of guide wires may allow the physician to select an appropriate guide wire for the patient, based on criteria such as patient vasculature structure or the size of the obstruction.

Figure 3A:
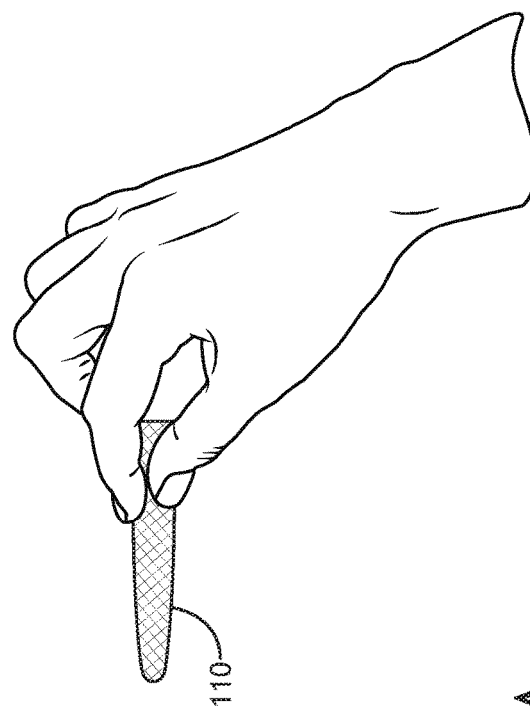
FIG. 3A illustrates the expandable member being loaded onto the guide wire for deployment through the guide catheter, in accordance with one or more embodiments of the present disclosure.
Figure 3B:
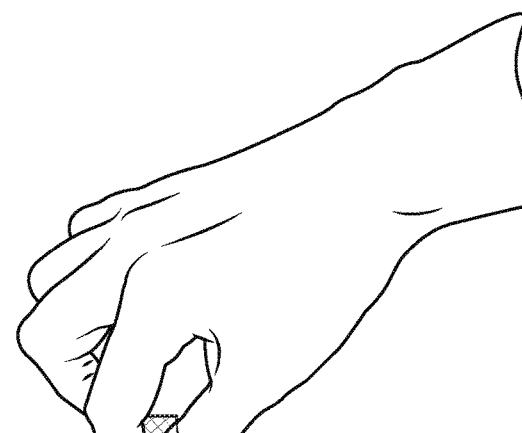
FIG. 3B illustrates the expandable member loaded onto the guide wire for deployment through the guide catheter, in accordance with one or more embodiments of the present disclosure.

FIGS. 3A through 3D illustrate the manner by which the expandable member 110, as described with reference to FIGS. 2A through 2I, can be inserted into and deployed through the guide catheter 106. For example, FIGS. 3A and 3B illustrate the expandable member 110 being loaded onto the guide wire 116 for deployment through the guide catheter 106. FIGS. 3C and 3D then illustrates the expandable member 110 being pushed along the guide wire 116 by the microcatheter 114. In this manner the expandable member 110 can be fed through the guide catheter 106, into the vasculature 102, and positioned proximate to and/or in contact with the stentriever 118 as previously discussed herein with reference to FIGS. 2D and 2E.

Referring generally to embodiments of the obstruction removal system 100 disclosed herein, the expandable member 110 may be configured to transition between a first configuration and a second configuration, or between a contracted state and an expanded state, in any number of ways, including, but not limited to, unsheathing (e.g., withdrawal of the microcatheter 114 or extension through the guide catheter 106), disengagement of locking members (e.g., wires, hooks, etc.) attached to the expandable member 110, use of shape memory alloys (e.g., Nitinol), or the like. It is envisioned that when the expandable member is in an expanded state, the expandable member may take up a substantial portion of the cross-section of the vasculature or the vessel wall 102.

In embodiments, the expandable member 110, the obstruction 108, and the stentriever 118 are withdrawn into the guide catheter 106 and removed from the vasculature. In some embodiments, the expandable member 110, the obstruction 108, and the stentriever 118 may be further withdrawn into the microcatheter 114. The expandable member 110 may surround at least a portion of the obstruction 108 to prevent dislodging and may also assist in compressing the obstruction 108 into the guide catheter 106 and/or the microcatheter 114 (e.g. by tension, cinching, crimping, etc.).

In some embodiments, an expandable member 110 may further include one or more features including, but not limited to, hooks. The hooks may attach to or make abrasive contact with a vessel wall when the expandable member 110 is in the expanded state; the hooks may also hold a portion of the obstruction 108 when the expandable member 110 at least partially surrounds the obstruction 108 prior to its removal.

Surrounding at least a portion of the obstruction 108 and/or stentriever 118 by the expandable member 110 may serve several functions including, but not limited to, reducing a likelihood that the stentriever 118 snags (e.g. on a vessel wall 102 or an opening of the guide catheter 106), reducing a profile of the obstruction 108 for removal through the guide catheter 106 and/or microcatheter 114, and/or securing the obstruction 108 to prevent dislodgement from the stentriever 118.

In embodiments, the expandable member 110 may comprise a wire mesh. Such a wire mesh may include wires made of a flexible material (e.g. nitinol, cobalt chromium, polymer mesh, or the like), where the wires (e.g. 16 to 288 or more wires), have a certain diameter (e.g. from 0.0007 inches to 0.0050 inches), and have certain material properties (e.g. strength, coefficient of friction with blood, resistance to plastic deformation, etc.) suitable for engaging the obstruction 108 and/or the stentriever 118. Furthermore, the wire mesh may include various sets of wires (e.g. support wires with larger diameters, wires to engage a vessel wall, wires to engage a portion of the obstruction or stentriever, radiopaque or radiodense wires, etc.).

Any number of the presently disclosed elements may be suitable for imaging by a non-invasive imaging technology (e.g. X-ray, CT scans, etc.). For instance, the guide catheter 106, guide wire 116, microcatheter 114, expandable member 110, stentriever 118, guide stops 104, base member 112, locking member 204, locking member 202, and/or any additional components may comprise radiodense or radiopaque material (e.g. titanium, tungsten, barium sulfate, or zirconium oxide) suitable for insertion in a human body.

It is to be understood that any number of components of the obstruction removal system 100 may be attached by any suitable means including, but not limited to, welding, adhesive, mechanical fastening, interference fittings, etc. For example, the base member 112 or locking member 204 may be attached to the expandable member 110 by such means.

Alternatively, or additionally, two or more of the components may be portions of a common structure (e.g., a common mold or print).

In some embodiments, the expandable member 110 is temporarily attached to the microcatheter 114. For example, the expandable member 110 may be configured to detach from the microcatheter 114 after locking member 204 engages locking member 202 or after base member 112 engages the one or more guide stops 104.

The locking members 202 and 204 and/or the base member 112 and guide stop(s) 104 may be configured to selectively engage and disengage. It is envisioned that the ability to selectively engage and disengage may provide advantages. For example, the ability to selectively disengage may allow for reusability of one or more of the components (e.g. expandable member 110, microcatheter 114, guide catheter 106, etc.). By way of another example, the ability to engage and disengage may provide increased functionality when inserting and removing components through the guide catheter 106 (e.g. fewer components translating through the guide catheter 106 at the same time).

It is envisioned that there may be multiple orders in which one or more devices of the obstruction removal system 100 are deployed. Factors for determining an order may include, but are not limited to, vasculature properties (e.g. vasculature size, vasculature geometries, branches of the vasculature, vasculature wall strength, etc.), blood pressure, blood flow direction, duration of operation (i.e. does patient require a reduced operating time for safety concerns), size of obstruction, or the configuration of the obstruction removal device.

Referring generally to FIGS. 1A through 1K, a method of removing an obstruction from a vasculature may include, but is not limited to, the steps of: deploying the guide catheter 106 through the patient's vasculature to a position near the obstruction 108, where the guide catheter 106 includes one or more guide stops 104 on an inner surface at the distal end of the guide catheter 106; inserting the expandable member 110 through the guide catheter 106 and (with a delivery tool 120) pushing the expandable member 110 up to the distal end of the guide catheter 106, so that a base member 112 attached to the expandable member 110 engages the guide stops 104; inserting the stentriever 118 attached to guide wire 116 within a microcatheter 114 and feeding the stentriever 118 through the guide catheter 106 using the microcatheter 114; deploying the stentriever 118 and the microcatheter 114 through the guide catheter 106, guide stops 104, and expandable member 110 up to the obstruction 108; withdrawing the microcatheter 114 to unsheathe the stentriever 118 to engage the obstruction 108 with the stentriever 118; withdrawing the stentriever 118 and the obstruction 108 by withdrawing (e.g., pulling) the guide wire 116, where the expandable member 110 surrounds at least a portion of the obstruction 108 and/or the stentriever 118 and transitions from an expanded state to a contracted state as the guide wire 116 with the stentriever 118 and obstruction 108 are pulled through the guide catheter 106 and removed from the vasculature.

Referring generally to FIGS. 2A through 2I, a method of removing an obstruction from a vasculature may include, but is not limited to, the steps of: deploying the guide catheter 106 through the patient's vasculature to a position near the obstruction 108; deploy the stentriever 118 in a microcatheter 114 through the guide catheter 106, out of a distal end of the guide catheter 106, and to a position proximate to the obstruction 108; pushing the microcatheter 114 and the stentriever 118 through/around the obstruction 108; withdraw the microcatheter 114 from the vasculature to unsheathe the stentriever 118 so that the stentriever 118 engages the obstruction 108; sliding the expandable member 110 onto the guide wire 116; sliding the expandable member 110 along the guide wire 116 through the guide catheter 106 using the microcatheter 114 to push the expandable member 110 until locking member 204 at the base of the expandable member 110 engages locking member 202 on the guide wire 116, the stentriever 118, or an inner surface of the guide catheter 106, thereby coupling the expandable member 110 to the guide wire 116, the stentriever 118, or the inner surface of the guide catheter 106; and removing the guide wire 116 from the vasculature to remove the stentriever 118 and the obstruction 108 from the vasculature, causing the expandable member 110 to surround at least one portion of the stentriever 118 and/or the obstruction 108 as the expandable member 110 inverts and transitions from an expanded state to a contracted state when the guide wire 116 is removed from the vasculature to remove the stentriever 118 and the obstruction 108 from the vasculature.

It is to be understood that implementations of the methods disclosed herein may include one or more of the steps described herein. Further, such steps may be carried out in any desired order and, in some implementations, two or more of the steps may be carried out simultaneously with one another. Two or more of the steps disclosed herein may be combined in a single step, and in some implementations, one or more of the steps may be carried out as two or more sub-steps. Further, other steps or sub-steps may be carried in addition to, or as substitutes to one or more of the steps disclosed herein.

It is also to be understood that usage of terminology in the present disclosure is not intended to be limiting. For example, as used herein, an "obstruction" may refer to any vascular obstruction, including but not limited to, a blood clot, plaque (e.g. fat, cholesterol, etc.), internal structure/growth, foreign object, or the like.

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An obstruction removal system, comprising:
   a guide catheter configured to be inserted within a vasculature;
   a guide wire having a distal end configured to be inserted within the guide catheter and disposed proximate to an obstruction in the vasculature;
   a stentriever disposed at the distal end of the guide wire, the stentriever configured to engage the obstruction in the vasculature;
   an expandable member configured to be slidably coupled to the guide wire, the expandable member being configured to transition between a contracted state and an expanded state, wherein the expandable member is configured to surround at least one portion of the stentriever and the obstruction as the expandable member transitions from the expanded state to the contracted state when the guide wire is removed from the vasculature to remove the stentriever and the obstruction from the vasculature;

a first locking member at a base of the expandable member; and a second locking member on an inner surface of the guide catheter at or near a distal opening of the guide catheter, wherein the first locking member at the base of the expandable member is configured to engage the second locking member on the inner surface of the guide catheter, thereby coupling the base of the expandable member to the inner surface of the guide catheter, when the expandable member is deployed out of the distal opening of the guide catheter, and wherein the first locking member is further configured to disengage from the second locking member when the guide wire is removed from the vasculature to remove the stentriever and the obstruction from the vasculature.

2. The obstruction removal system of claim 1, wherein the first and second locking members comprise snap-fit connectors.

3. The obstruction removal system of claim 1, wherein the first and second locking members comprise cooperatively threaded connectors.

4. The obstruction removal system of claim 1, wherein the first and second locking members comprise magnetic connectors.

5. The obstruction removal system of claim 1, further comprising:

a delivery tool configured to slide the expandable member through the guide catheter until the first locking member engages the second locking member.

6. The obstruction removal system of claim 1, wherein the first and second locking members comprise guide stops.

7. A method for removing an obstruction from a vasculature, comprising:

inserting a guide catheter within a vasculature;

extending a guide wire through the guide catheter so that a distal end of the guide wire is disposed proximate to the obstruction in the vasculature;

engaging at least one portion of the obstruction in the vasculature with a stentriever disposed at the distal end of the guide wire;

sliding an expandable member through the guide catheter until a first locking member at a base of the expandable member engages a second locking member on an inner surface of the guide catheter at or near a distal opening of the guide catheter, thereby coupling the base of the expandable member to the inner surface of the guide catheter, when the expandable member is deployed out of the distal opening of the guide catheter, the expandable member being configured to transition between a contracted state and an expanded state; and removing the guide wire from the vasculature to remove the stentriever and the obstruction from the vasculature, wherein the expandable member is configured to surround at least one portion of the stentriever and the obstruction as the expandable member transitions from the expanded state to the contracted state when the guide wire is removed from the vasculature to remove the stentriever and the obstruction from the vasculature, and wherein the first locking member is disengaged from the second locking member when the guide wire is removed from the vasculature to remove the stentriever and the obstruction from the vasculature.

8. The method of claim 7, wherein the first and second locking members comprise snap-fit connectors.

9. The method of claim 7, wherein the first and second locking members comprise cooperatively threaded connectors.

10. The method of claim 7, wherein the first and second locking members comprise magnetic connectors.

11. The method of claim 7, wherein the first and second locking members comprise guide stops.

* * * * *